United States Patent
Bae

(10) Patent No.: US 6,483,090 B1
(45) Date of Patent: Nov. 19, 2002

(54) GLARE PROTECTING DEVICE AND METHOD OF CONTROLLING THEREOF

(75) Inventor: Young Dawn Bae, Suwon (KR)

(73) Assignee: Otos Co., Ltd. (KR)

( * ) Notice: Subject to any disclaimer, the term of this patent is extended or adjusted under 35 U.S.C. 154(b) by 0 days.

(21) Appl. No.: 09/465,964

(22) Filed: Dec. 17, 1999

(30) Foreign Application Priority Data

Dec. 29, 1998 (KR) .............................. 98-60013
Apr. 30, 1999 (KR) .............................. 99-15627

(51) Int. Cl.[7] ............................................. G01J 1/20
(52) U.S. Cl. ................ 250/201.1; 250/205; 250/214 B; 250/216; 2/8; 349/14; 359/601
(58) Field of Search .......................... 250/205, 214 AL, 250/214 R, 215, 216, 231.1, 229, 214 RC, 214 B, 201.1, 554; 2/8; 349/13, 14, 33; 359/265, 601, 603, 604

(56) References Cited

U.S. PATENT DOCUMENTS

| | | | |
|---|---|---|---|
| 5,252,817 A | * | 10/1993 | Fergason et al. ............ 250/205 |
| 5,315,099 A | * | 5/1994 | Gunz et al. ............... 250/201.1 |
| 5,444,232 A | * | 8/1995 | Gunz et al. ..................... 2/8 |
| 5,751,258 A | | 5/1998 | Fergason et al. |
| 5,793,449 A | | 8/1998 | Lagerwall |
| 5,825,441 A | | 10/1998 | Hornell et al. |
| 5,857,215 A | | 1/1999 | Fergason et al. |
| 5,880,793 A | | 3/1999 | Gunz et al. |
| 5,930,047 A | | 7/1999 | Gunz et al. |
| 5,959,705 A | | 9/1999 | Fergason |
| 6,097,451 A | * | 8/2000 | Palmer et al. ................ 349/14 |

* cited by examiner

Primary Examiner—Stephone Allen
(74) Attorney, Agent, or Firm—Cantor Colburn LLP

(57) ABSTRACT

A glare protecting device and a method of controlling thereof for protecting a worker's eyes from a light comprising: a temperature detector for generating a temperature detecting signal by detecting ambient temperature; a controller for generating a starting signal having a starting time in response to the temperature detecting signal, and for generating a temperature compensating signal corresponding to the temperature detecting signal; a driving means for generating a starting voltage in response to the temperature compensating signal, and for generating an initial driving signal having a starting voltage in response to the starting signal; and a glare protecting plate which is started corresponding to the initial driving signal.

8 Claims, 5 Drawing Sheets

GLARE PROTECTING DEVICE AND METHOD OF CONTROLLING THEREOF

BACKGROUND OF THE INVENTION

1. Field of the Invention

The present invention relates to a glare protecting device and a method of controlling thereof, more particularly, for improving the response speed of a glare protecting plate in accordance with ambient temperature.

2. Description of the Prior Art

A glare protecting device protects a worker's eyes from light generated in using a welding or cutting torch.

U.S. Pat. No. 5,315,099 discloses a glare protecting device comprising a glare protecting plate, an electronic circuit connected to the glare protecting plate for applying an electronic operating voltage thereto, and a light sensor which detects a light and applies a signal corresponding to the detected signal to the electronic circuit.

U.S. Pat. No. 5,444,232 discloses a glare protecting device comprising a glare protecting plate, an optical signal detector for producing a dimming signal, an evaluating circuit for controlling the glare protecting plate, and a controller for controlling the brightening time of the glare protecting plate and detecting the intensity of the light impinging on the light sensor. The controller is connected to a timing generator to detect the duration of the dimming signal produced by the detector, and comprises means to interlink the acquired data with respect to logic and/or time.

The device disclosed in U.S. Pat. No. 5,444,232 detects the light intensity or the amount of light, and the welding duration, and interconnects these parameters with respect to logic and/or time by means of a suitable controller, thereby optimizing the brightening time.

The conventional glare protecting device described above uses a liquid crystal display as a glare protecting plate. However, because of its inherent characteristics, a liquid crystal display has a slow response speed in low temperatures.

SUMMARY OF THE INVENTION

One object of the present invention is to provide a glare protecting device which can improve the response speed of a glare protecting plate in reaction to temperature by detecting ambient temperature, in order to solve the problem of the prior art mentioned above.

Another object of the present invention is to provide a method of controlling a glare protecting device to accomplish the above object.

To accomplish the above objects, pursuant to the present invention, a glare protecting device for protecting a worker's eyes from a light is provided which comprises:

a temperature detector for generating a temperature detecting signal by detecting ambient temperature;

a controller for generating a starting signal having the starting time corresponding to the temperature detecting signal, and for generating a temperature compensating signal corresponding to the temperature detecting signal;

a driving means for generating a starting voltage in response to the temperature compensating signal, and an initial driving signal having the starting voltage in response to the starting signal; and a glare protecting plate which is started responding to the initial driving signal.

To accomplish another of the above objects, pursuant to the present invention, a method of controlling a glare protecting device is provided comprising:

a temperature detector for generating a temperature detecting signal by detecting ambient temperature;

a glare protecting plate for protecting a worker's eyes from a light; and a controller for controlling the drive of the glare protecting plate by inputting the temperature detecting signal, the method comprises steps of:

generating a starting signal having a starting time, and a temperature compensating signal operating in response corresponding to the temperature detecting signal;

generating a starting voltage in response to the temperature compensating signal, and an initial driving signal having the starting voltage in response to the starting signal; and starting the glare protecting plate in response to the initial driving signal.

Further objects and advantage of the present invention can be more fully understood from the following detailed description taken in conjunction with the accompanying drawings.

DETAILED DESCRIPTION OF THE INVENTION

Figure 1:
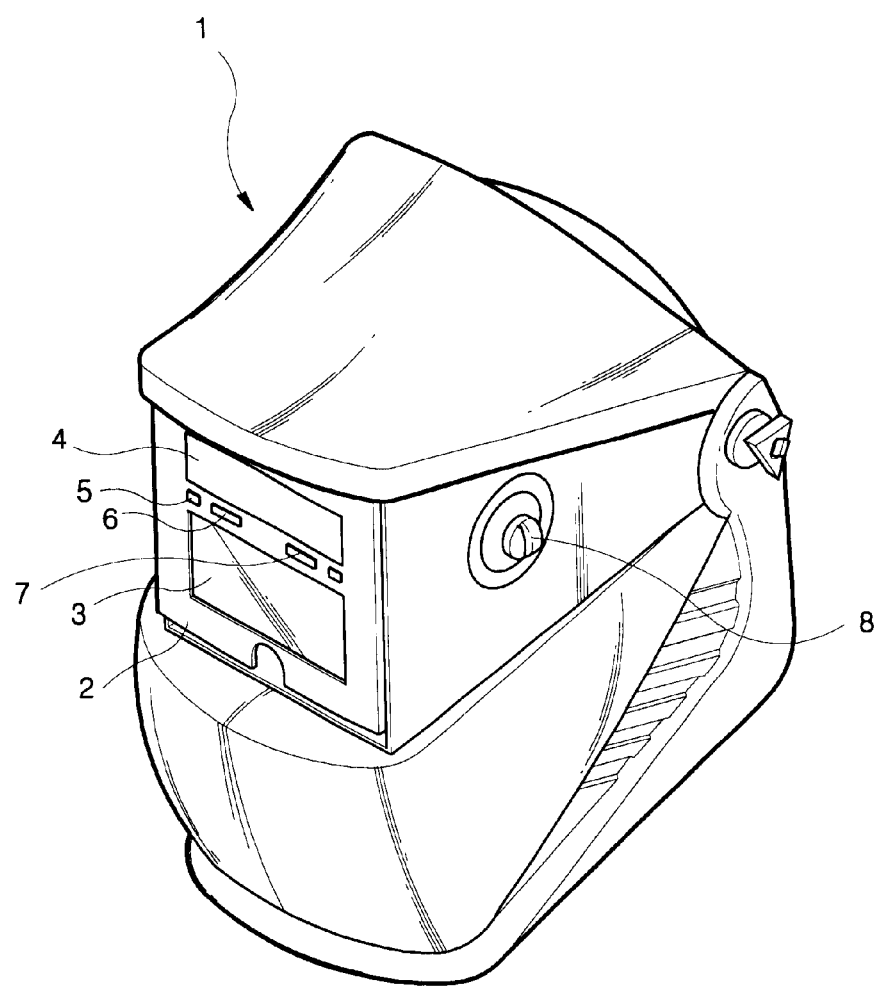
FIG. 1 illustrates a protective mask having a glare protecting device.

FIG. 1 illustrates a protective mask having a glare protecting device. The protective mask 1 comprises, a glare protecting device 2, a glare protecting plate 3, a solar cell 4, a light sensor 5, a temperature sensor 6, an antenna 7, and an intensity control switch 8.

As shown in FIG. 1, the glare protecting device 2 is disposed at the front side of the protective mask 1. The glare protecting device 2 has a controller (not shown) to regulate a glare protecting plate 3 to protect a worker's eyes from a high intensity light. The glare protecting plate 3 is transparent when a light is not applied thereto, but it is dimmed when a light impinges thereon. The solar cell 4 generates a voltage in the event that ambient light is applied thereto. The light sensor 5 detects a light in the event that ambient light is applied thereto. The temperature sensor 6 detects ambient temperature. The antenna 7 receives an ambient electromagnetic wave. The intensity control switch 8 is composed of a volume switch and controls the dimming intensity of the glare protecting plate 3.

Accordingly, the glare protecting device 2 shown in FIG. 1 detects ambient light and electromagnetic wave by means of the light sensor 5 and the antenna 7. Then, the controller (not shown) receives input from the light sensor 5 and the antenna 7 and controls operation of glare protecting plate 3 which is dimmed in order to protect eyes of a worker wearing the protective mask 1. Also, in the event that the temperature detected by the temperature sensor 6 is low, the controller (not shown) accelerates the response time of the glare protecting plate 3.

Figure 2:
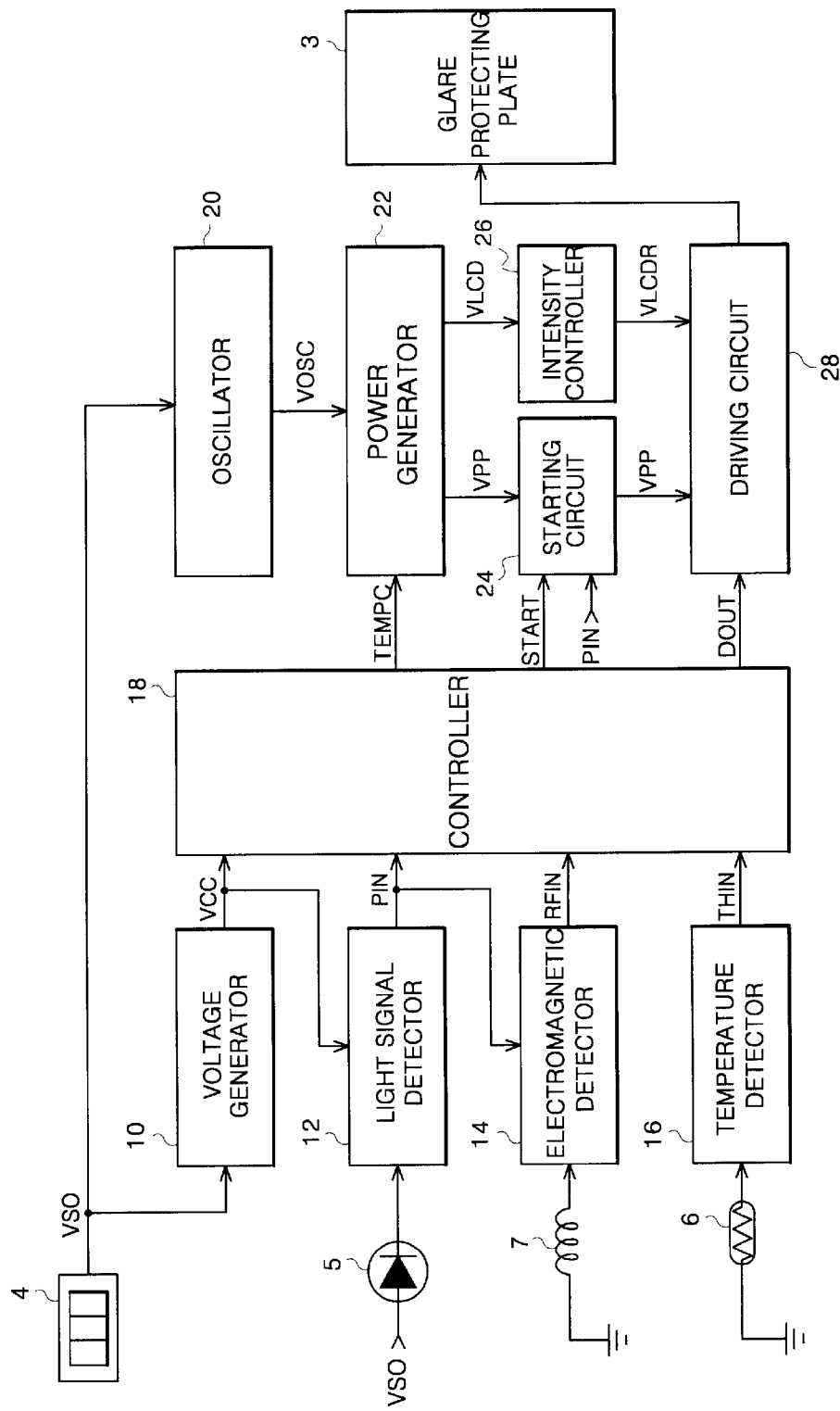
FIG. 2 a block diagram of a glare protecting device according to the present invention.

FIG. 2 is a block diagram of a glare protecting device, comprising a voltage generator 10, a light signal detector 12, an electromagnetic wave detector 14, a temperature detector 16, a controller 18, an oscillator 20, a power generator 22, a starting circuit 24, an intensity controller 26, and a driving circuit 28.

Referring to FIG. 2, a solar cell 4, a light sensor 5, an antenna 7, a temperature sensor 6, and a glare protecting plate 3 have the identical numerals with those of FIG. 1. In a preferred embodiment, the light sensor 5 can be composed of a photodiode, the antenna 7 can be a coil, and the temperature sensor 6 can be a thermistor.

Functions of blocks illustrated in FIG. 2 are described as below.

The solar cell 4 generates a voltage (VSO) when light is applied thereto. The voltage generator 10 inputs the voltage (VSO) and generates a voltage (VCC). The voltage generator 10 is a charging circuit including a lithium cell (not shown) as a charging battery, and outputs the charged voltage VCC to the controller 18.

When voltage VSO is generated, the light signal detector 12 detects the ambient light by means of the light sensor 5 and generates a light detecting signal PIN. The light signal detector 12 generates the light detecting signal PIN when a light emitted by the welding or the cutting torch is detected by the light sensor 5. It is preferred that the light signal detector 12 comprises a filter and an amplifier for detecting only a light signal of an effective band.

Accordingly, the solar cell 4 and the light signal detector 12 are optical detectors for detecting the ambient light.

The electromagnetic wave detector 14 detects a frequency signal of an effective band and generates an 15 electromagnetic wave detecting signal RFIN when an electromagnetic wave is inputted through the antenna 7. It is preferred that the electromagnetic wave detector 14 comprises a resonator, a filter and a comparator for receiving a specific frequency band from an electromagnetic wave received from the antenna 7. Accordingly, in the event that the electromagnetic wave detector 14 detects an electromagnetic wave generated in the welding and the cutting torch, it generates the electromagnetic wave detecting signal RFIN.

The temperature detector 16 generates a temperature detecting signal THIN corresponding to ambient temperature is detected by a thermistor 6.

Accordingly, the electromagnetic wave detector 14 and the temperature detector 16 are non-optical detectors which detect the ambient frequency and temperature.

The controller 18 inputs and processes the light detecting signal PIN, the electromagnetic wave detecting signal RFIN, and the temperature detecting signal THIN outputted from the light signal detector 12, the electromagnetic wave detector 14, and the temperature detector 16, and generates a starting signal START for controlling the starting circuit 24 and a driving control signal DOUT for controlling the driving circuit 28. The controller 18 generates a temperature compensating signal TEMPC in the event that the temperature detecting signal THIN is less than a predetermined value, and generates a starting signal START for controlling the starting circuit 24 by inputting and processing the temperature detecting signal THIN. It is preferred that the controller is a microcomputer.

The oscillator 20 inputs the voltage VSO and generates an oscillating voltage VSO. The oscillating voltage is a signal of a pulse type.

The power generator 22 inputs and boosts the oscillating voltage VSO, and generates a starting voltage VPP and a driving voltage VLCD. The power generator 22 boosts the starting voltage VPP in the event that the temperature compensating signal TEMPC is generated. It is preferred that the power generator 22 includes a voltage doubler rectifier circuit composed of a capacitor.

The starting circuit 24 outputs the starting voltage VPP in response to the starting signal START or the light detecting signal PIN. At this time, the controller 18 controls the starting time of the starting signal START.

The intensity controller 26 controls the driving voltage VLCDR by controlling the driving voltage VLCD by means of the intensity control switch 8.

The driving circuit 28 selects a voltage outputted from the starting circuit 24 in response to the starting signal START or the light detecting signal PIN at the time of starting. And at the time of driving, the driving circuit 28 selects the driving voltage VLCDR in response to the driving control signal DOUT and generates a driving signal for driving the glare protecting plate 3. At this time, the driving signal is a square-wave signal.

In an embodiment wherein the glare protecting plate 3 is composed of a liquid crystal display device, the driving circuit 28 selects the driving voltage VLCDR in response to the driving control signal DOUT, and selects the starting voltage VPP in response to the starting signal START or the light detecting signal PIN to generate a driving signal.

Accordingly, the driving circuit 28 selects and outputs a high starting voltage VPP at the time of starting of the glare protecting plate 3. After starting the glare protecting plate 3, the driving circuit 28 selects and outputs the driving voltage VLCDR lower than the starting voltage VPP.

Accordingly, the glare protecting device of the present invention controls the starting time and the starting voltage of the starting signal START for starting the glare protecting plate according to temperature, in order to improve the response speed of the glare protecting plate.

Figure 3:
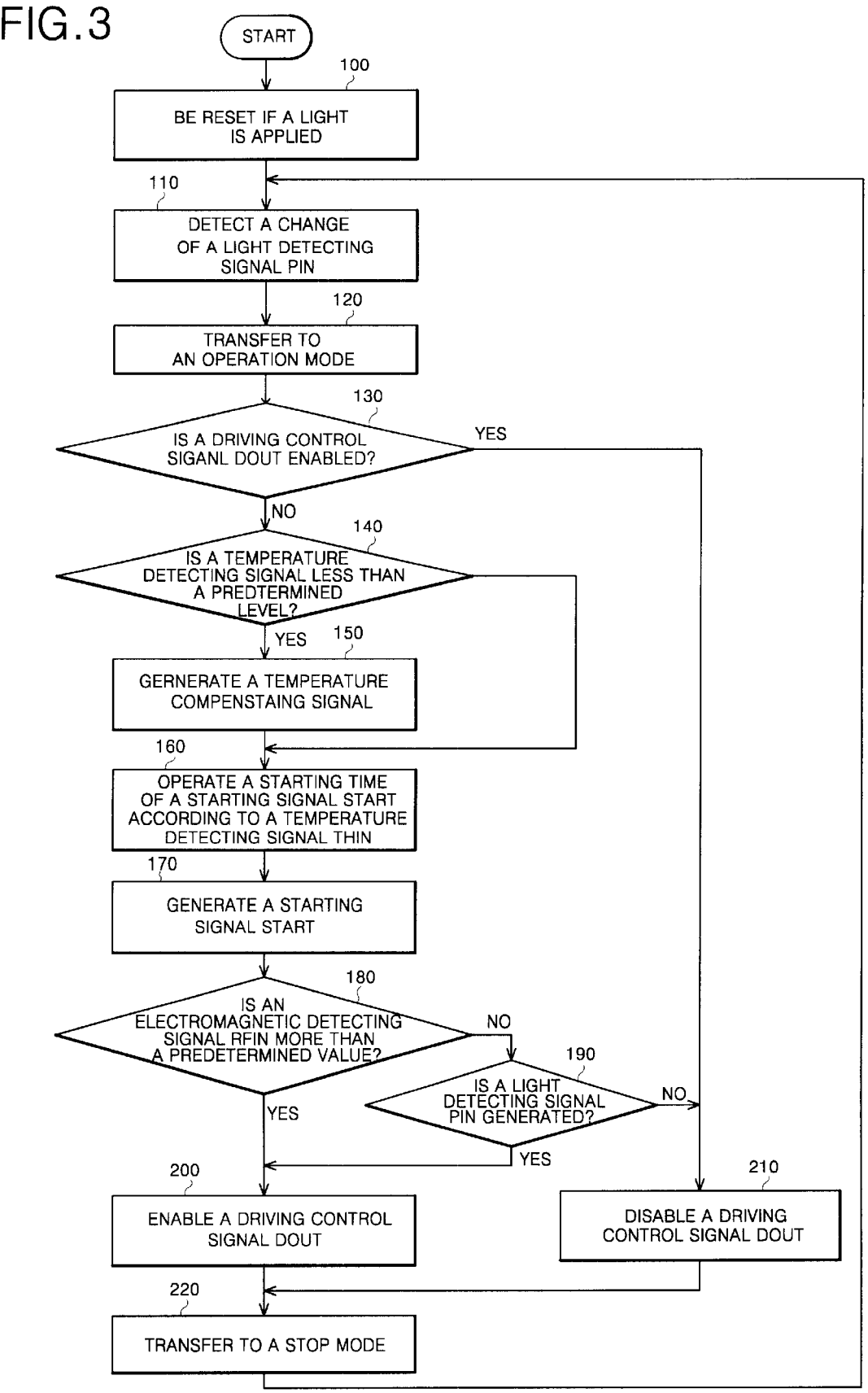
FIG. 3 is a flow chart depicting an operation of a controller of the glare protecting device of FIG. 2.

FIG. 3 is a flow chart explaining operation of a controller for the glare protecting device according to the present invention. The operation of the glare protecting device of the present invention is described as below referring to FIG. 3.

The solar cell 4 generates a voltage VSO in the event that a light is applied thereto, and a voltage generator 10 produces a voltage VCC. The controller 18 is reset for processing a signal to be inputted when the voltage VCC is applied thereto (Step 100).

The light sensor 5 is turned on in the event that the voltage VSO is generated. The light signal detector 12 detects a light signal of an effective frequency band in signals applied from the light sensor 5, and generates the light detecting signal PIN. The controller 18 detects a change of the light detecting signal PIN(Step 110).

Accordingly, when the light detecting signal PIN stored in an internal resistor (not shown) of the controller 18 is "1" when the controller 18 is reset by applying a power supply thereto, and the light detecting signal PIN is "0" when the light signal detector 12 detects a light signal, the controller 18 detects that the light detecting signal PIN changes to "0". Of course, a reverse change can be detected. Accordingly, the controller 18 detects two cases: that ambient light disappears, and that the ambient light appears.

The controller 18 is shifted to an operating mode in case that the light detecting signal PIN is changed (Step 120).

The controller 18 determines whether the driving control signal DOUT is in a enable state or not (Step 130).

As a result of the determination of Step 130, in the event that the driving control signal DOUT is in an enable state, the driving control signal DOUT is disabled at Step 210.

As a result of the determination of Step 130, in the event that the driving control signal DOUT is not in an enable state, the controller 18 determines whether the temperature detecting signal THIN inputted from the temperature detector 16 is less than a predetermined level (Step 140).

As a result of the determination of Step 140, in the event that the temperature detecting signal indicates a low temperature, the controller 18 generates the temperature compensating signal TEMPC (Step 150). The power generator 22 boosts the starting voltage VPP and generates the boosted starting voltage VPP in case that the temperature compensating signal TEMPC is inputted. On the contrary, in case that the result of Step 140 is not positive, the process proceeds to Step 160.

The controller 18 regulates the starting time of the starting signal START according to the temperature detecting signal THIN.

That is, in the event that the temperature detecting signal THIN appears to indicate a low temperature, the controller 18 boosts the starting voltage VPP by generating the temperature compensating signal TEMPC for compensating temperature. Also, the controller 18 regulates the starting time of the starting signal START according to the temperature detecting signal THIN. Accordingly, the glare protecting plate is rapidly operated even at low temperatures.

The characteristic response speed of a liquid crystal glare protecting plate 3 is rapid in high temperature and slow in low temperature. Therefore, in prior art embodiments, the glare protecting plate performs a light shielding operation only after the welding light already has been is transmitted to a worker's eyes, since its response speed is delayed during the first stage of a welding operation at low ambient temperatures. However, the controller 18 of the present invention performs operations of Step 140, Step 150 and Step 160 in order to solve this delay problem of the prior art.

The controller 18 outputs the starting signal START to the starting circuit 24 (Step 170). The starting circuit 24 generates the voltage VPP in response to the light detecting signal PIN of the light signal detector 12 or the starting signal START. The driving circuit 28 inputs the voltage VPP and drives the glare protecting plate 3. When the starting signal START or the light detecting signal PIN is not generated, the driving circuit 28 inputs the voltage VLCDR and drives the glare protecting plate 3.

The controller 18 determines whether the electromagnetic wave detecting signal RFIN applied from the electromagnetic wave detector 14 is higher than a predetermined value or not (Step 180). The controller 18 inputs the electromagnetic wave detecting signal RFIN and decides whether the welding can be continued or not. Accordingly, the electromagnetic wave of between 2 KHz and 400 KHz band as well as a light signal is generated according to the kind of a welding machine using arc, gas or etc. during the welding.

The controller 18 enables the driving control signal DOUT in the event that the electromagnetic wave detecting signal RFIN is higher than a predetermined value (step 200).

On the contrary, in the event that the electromagnetic wave detecting signal RFIN is not higher than a predetermined value, the controller 18 determines whether the light detecting signal PIN is generated or not (Step 190).

In the event that the light detecting signal PIN is generated, the process proceeds to step 200. In the event that the light detecting signal PIN is not generated, the process proceeds to step 210.

In step 180 which determines whether the electromagnetic wave detecting signal RFIN is generated and in step 190 which determines whether the light detecting signal PIN is generated, the controller 18 determines that the welding is being performed and enables the driving control signal DOUT in the event that the electromagnetic wave detecting signal RFIN is higher than a predetermined value or the light detecting signal PIN is generated.

After performing the step 200 or step 210, the controller 18 is shifted to a stop mode (step 220). The controller 18 repeatedly performs operations of the above-described steps.

Accordingly, the glare protecting device and the method of controlling thereof controls a starting time of a glare protecting plate according to temperature by detecting ambient temperature. The device boosts a starting voltage VPP by generating a temperature compensating signal in case that ambient temperature is less than a predetermined level, and then generates the boosted starting voltage. Thereby, the glare protecting device can improve the response speed of the glare protecting plate.

Figure 4:
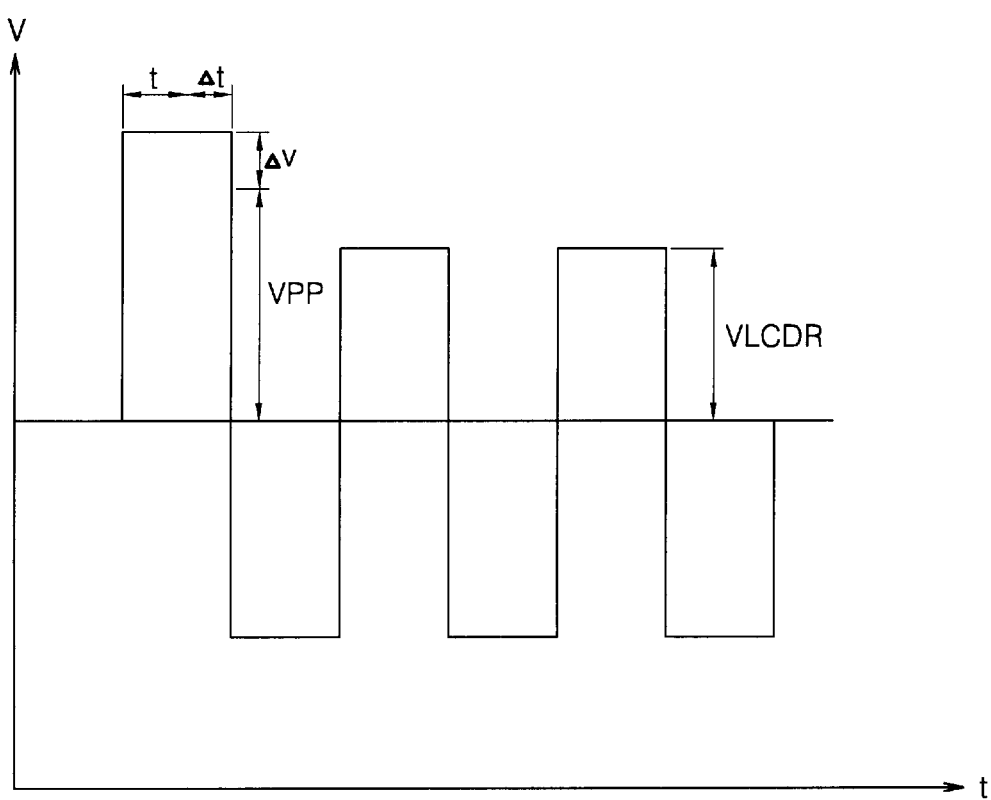
FIG. 4 illustrates an output waveform of a driving circuit of the glare protecting device according to the present invention.

FIG. 4 illustrates an output waveform of a driving circuit of the glare protecting device according to the present invention, showing a horizontal axis as time and a vertical axis as a voltage.

In the event that the temperature detecting signal THIN is less than a predetermined level, the starting time t of the starting signal is controlled to the starting time t+Δt, and the starting voltage VPP of the starting signal is controlled to the starting voltage VPP+ΔV.

As described above, the controller 18 operates the variable time Δt of the starting signal START by inputting the temperature detecting signal, and generates the temperature compensating signal TEMPC in the event that the temperature detecting signal THIN is less than a predetermined level. The power generator 22 varies and generates the variable voltage ΔV according to the temperature compensating signal TEMPC.

For example, in the event that the controller detects a temperature decrease of 1° C. from a reference temperature of 0° C., the response speed of a glare protecting plate can be improved in this manner of increasing the starting time of a driving signal which is applied the glare protecting plate by about 1 ms, or increasing the starting voltage by about 0.5V.

The starting time of the starting signal START is controlled not to be more than 80% of a reference time that starts the glare protecting plate 3, or not to be more than 50% of a reference voltage. In the event that the starting time and the starting voltage exceed the maximum allowable reference of the glare protecting plate 3, the glare protecting device including the glare protecting plate 3 may be damaged. Therefore, it is preferred that the acceleration of the starting time and the increase of the starting voltage are controlled not to be more than 30%, respectively.

Figure 5:
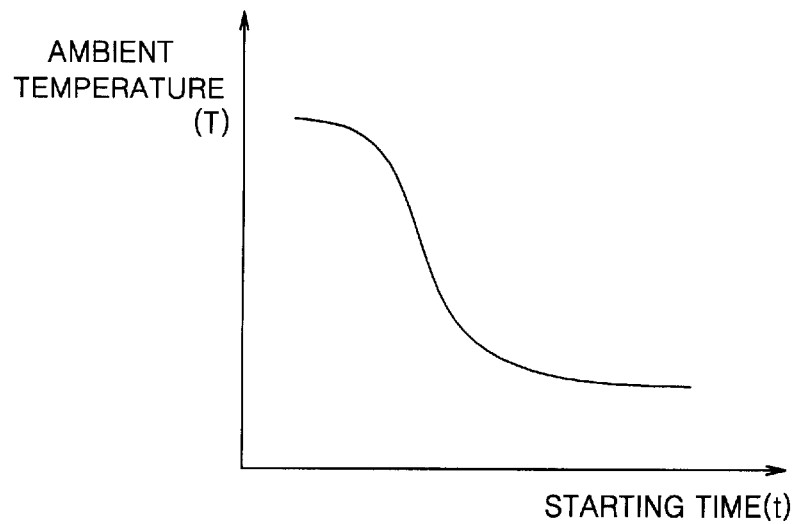
FIG. 5 is a graph showing the relationship between ambient temperature T and a starting time t of the glare protecting device according to the present invention.

FIG. 5 is a graph showing the change of a starting time t according to ambient temperature T in the glare protecting device of the present invention. As shown in FIG. 5, the starting time of the starting signal START is increased in accordance with the falling of ambient temperature.

Figure 6:
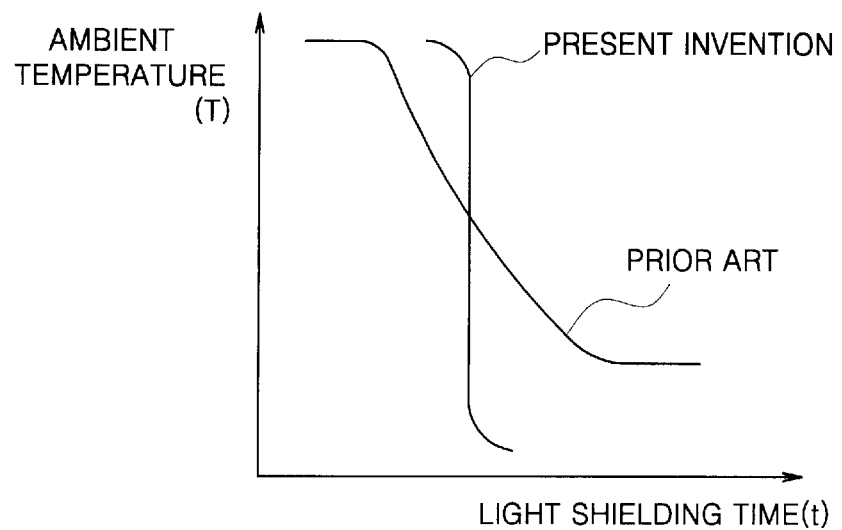
FIG. 6 is a graph showing the relationship between ambient temperature T and a light shielding time t of glare protecting devices according to the present invention in comparison to the prior art.

FIG. 6 is a graph showing the change of a light shielding time t according to ambient temperature T in the glare protecting devices of the present invention as compared to the prior art.

As known in FIG. 6, the light shielding time t is increased in proportion to the falling of ambient temperature T in the prior art. But, in the present invention, the light shielding time t is almost unaffected by ambient temperature T.

According to the present invention, the response speed of the glare protecting plate does not vary in response to ambient temperature by incorporating a process for changing a starting time and/or a starting voltage of a driving signal for driving the glare protecting plate according to the change of ambient temperature.

While this invention has been particularly shown and described with reference to preferred embodiments thereof, it will be understood by those skilled in the art that various changes in form and details may be made therein without departing from the spirit and scope of the invention. The invention may be embodied in other specific forms without departing from the spirit or essential characteristics thereof. The method of controlling a starting time and a starting voltage according to ambient temperature is applicable to other kind of a glare protecting device. The present embodiment is therefore to be considered in all respects as illustrative and not restrictive, the scope of the invention being indicated by the appended claims rather than by the foregoing description and all changes which come within the meaning and range of equivalency of the claims are therefore intended to be embraced therein.

What is claimed is:

1. A glare protecting device for protecting a worker's eyes from a light, comprising:

a glare protecting plate, an optical transmission of which is adjusted by a driving voltage supplied depending on an ambient temperature;

a temperature sensor for generating a temperature signal by detecting the ambient temperature;

a controller for generating a starting signal for triggering a starting voltage which decreases the optical transmission of said glare protecting plate during a predetermined starting time, wherein the starting signal comprises a duration determining the duration of the starting time in response to said temperature signal; for generating a temperature compensating signal corresponding to said temperature signal; and for generating a driving control signal controlling a continuous operation of said glare protecting plate; and a driving means for operating said glare protecting plate, wherein said driving means inputs said starting voltage in response to said starting signal or inputs a driving voltage in response to said driving control to said glare protecting plate;

wherein a voltage level of said starting voltage is controlled by said temperature compensating signal, so that said starting voltage is increased according to a falling of the ambient temperature and does not exceed more than 30% of a reference starting voltage with which said glare protecting plate is operated at a non-changed ambient temperature.

2. The glare protecting device of claim 1, wherein said duration of the starting time, at which the optical transmission of said glare protecting plate is decreased, is increased in response to the falling of ambient temperature.

3. The glare protecting device of claim 1, wherein said duration of the starting time is controlled not to exceed more than 30% of the reference starting time at which said glare protecting plate is operated at a non-changed ambient temperature.

4. The glare protecting device of claim 1, wherein said glare protecting plate comprises a liquid crystal display.

5. A method of controlling a dimming time of a glare protecting device comprising:

a temperature sensor for generating a temperature signal by detecting an ambient temperature;

a glare protecting plate, an optical transmission of which is adjusted by a driving voltage supplied depending on the ambient temperature; and a controller for adjusting the optical transmission of said glare protecting plate in response to said temperature signal, said method comprising:

generating a temperature compensating signal by said controller, when said temperature signal indicates that the ambient temperature is lower than a predetermined temperature;

generating a starting signal with a duration for triggering a starting voltage with the duration which is controlled in response to said temperature signal;

generating a starting voltage corresponding to said temperature compensating signal;

inputting said starting voltage as a driving voltage to said glare protecting plate in response to said starting signal of said controller; and decreasing the optical transmission of said glare protecting plate in response to said starting voltage.

6. The method of claim 5, wherein said glare protecting plate comprises a liquid crystal display.

7. The glare protecting device of claim 5, wherein said duration of the starting time, at which the optical transmission of said glare protecting plate is decreased, is increased in response to the falling of ambient temperature.

8. The glare protecting device of claim 5, wherein said duration of the starting time is controlled not to exceed more than 30% of the reference starting time at which said glare protecting plate is operated at a non-changed ambient temperature.

* * * * *